US008663604B2

(12) United States Patent
Nguyen et al.

(10) Patent No.: US 8,663,604 B2
(45) Date of Patent: Mar. 4, 2014

(54) METHOD FOR MEASURING NEUROTRANSMITTERS IN VIVO

(75) Inventors: Quoc-Thang Nguyen, San Diego, CA (US); David Kleinfeld, La Jolla, CA (US); Lee F. Schroeder, La Jolla, CA (US)

(73) Assignee: The Regents of the University of California, Oakland, CA (US)

(*) Notice: Subject to any disclaimer, the term of this patent is extended or adjusted under 35 U.S.C. 154(b) by 322 days.

(21) Appl. No.: 12/676,912

(22) PCT Filed: Sep. 4, 2008

(86) PCT No.: PCT/US2008/075240
§ 371 (c)(1), (2), (4) Date: Jul. 9, 2010

(87) PCT Pub. No.: WO2009/032914
PCT Pub. Date: Mar. 12, 2009

(65) Prior Publication Data

US 2010/0278746 A1 Nov. 4, 2010

Related U.S. Application Data

(60) Provisional application No. 60/970,449, filed on Sep. 6, 2007.

(51) Int. Cl.
*A61B 5/00* (2006.01)
*A61B 5/1495* (2006.01)

(52) U.S. Cl.
USPC ............. 424/9.6; 435/325; 435/7.1; 435/7.95

(58) Field of Classification Search
None
See application file for complete search history.

(56) References Cited

U.S. PATENT DOCUMENTS 7,258,687 B2 8/2007 Friedman et al.
2007/0299331 A1 12/2007 Friedman et al.

OTHER PUBLICATIONS

Okumoto et al., PNAS, 102[24]: 8740-8745, Jun. 2005.*
Mank et al., Biophysical Journal, 90:1790-1796, Mar. 2006.*
Kawaja et al., J Comp Neurol., 317(1):102-106, Mar. 1992.*
Levene et al., J. Neurophysiology, 91:1908-1912, Dec. 2003.*
Hasan et al., PloS Biology, 2(6):763-775, Jun. 2004.*
Garaschuk et al., Cell Calcium, 42:351-361, 2007.*
Feng et al., J Biol Chem, 273(17):10755-10762, Apr. 24, 1998.*
Kleinfeld,David, "Application of Spectral Methods to Representative Data Sets in Electrophysiology and Functional Neuroimaging", 2008, Chapter from Short Course #3 titled "Neural Signal Processing: Quantitative Analysis of Neural Activity", organized by Partha P. Mitra, Nov. 14, 2008.
Kleinfeld, David & Griesbeck, Oliver, "From Art to Engineering: The Rise of In Vivo Mammalian Electrophysiology via Genetically Targeted Labeling and Non-Linear Imaging", 2005, PLoS Biology, vol. 3, Issue 10, pp. 1685-1689, Oct. 2005.
Nguyen, Q.-T., et al., "Pioneering Applications of Two-Photon Microscopy to Mammalian Neurophysiology", 2008, Chapter 28 of "Handbook of Biomedical Nonlinear Optical Microscopy", Editors Barry R. Masters and Peter So, Oxford University Press.
Mank, Marco, et al., "A FRET-Based Calcium Biosensor with Fast Signal Kinetics and High Fluorescence Change", 2006, Biophysical Journal, vol. 90, pp. 1790-1796, Mar. 2006.

* cited by examiner

*Primary Examiner* — Daniel E Kolker
*Assistant Examiner* — Stacey N MacFarlane
(74) *Attorney, Agent, or Firm* — Eleanor M. Musick; Procopio, Cory, Hargreaves & Savitch LLP

(57) ABSTRACT

A method is provided for in vivo detection of a biochemical substance in an animal by culturing neurofluocytes that stably express a receptor of the biochemical substances by transfecting cells with cDNA of the receptor and a tag that will emit a detectable energy in the presence of the biochemical substance, implanting the neurofluocyte into the animal's brain; and detecting the energy emission of the tag. In a first embodiment, the biochemical substance is a neurotransmitter, the tag is a fluophore, and the step of detecting includes forming an opening in the animal's skull and optically detecting fluorescent emissions using a two-photon laser scanning microscope. Multiple biochemical substances can be simultaneously detected by culturing neurofluocytes that express different receptors and have different fluophor tags that produce fluorescent signals at distinguishable wavelengths.

20 Claims, 4 Drawing Sheets

METHOD FOR MEASURING NEUROTRANSMITTERS IN VIVO

RELATED APPLICATIONS

This application claims the priority of PCT Application No. PCT/US2008/075240, filed Sep. 4, 2008, and U.S. Provisional Application No. 60/970,449, filed Sep. 6, 2007, both of which are incorporated herein by reference in their entirety.

GOVERNMENT RIGHTS

This invention was made with government support under Grant No. MH071566, awarded by the National Institute of Mental Health (NIMH) and Grant No. EB003832, awarded by the National Institute for Biomedical Imaging and Bioengineering (NIBIB), both of the National Institutes of Health. The government has certain rights in the invention.

SEQUENCE LISTING

This application contains a Sequence Listing which has been submitted electronically as a pdf image to the U.S. Receiving Office via the USPTO EFS-Web, and is hereby incorporated by reference in its entirety. A computer readable version with content identical to the pdf image is also submitted herein.

FIELD OF THE INVENTION

The present invention is directed to a method for detecting neuroactive substances in live tissue. In particular, the method is designed to measure levels of biochemicals in live brain which were, until now, difficult to detect with sufficient specificity, sensitivity or temporal resolution.

BACKGROUND OF THE INVENTION

In the brain, neurons communicate with other neurons or non-neuronal cells mostly by sending or sensing neurotransmitters or neuromodulators. The ability to detect these compounds in the live brain is essential to understanding brain physiology. Furthermore, the development of methods to measure the amount of neurotransmitters and neuromodulators in vivo is critical to study the large number of pathologies associated with abnormal levels of extracellular signaling molecules in the brain.

In vivo monitoring techniques for neurotransmitters or neuromodulators measure changes in the concentration of specific substances in the extracellular compartment of selected brain regions resulting from the activity of neuronal assemblies. The two principal techniques used in neurotransmitter or neuromodulator monitoring in the live brain are microdialysis and voltammetry.

Microdialysis-based methods consist of implanting a cannula, for instance, inside the brain, to collect submicroliter volumes of cerebrospinal fluid at regular intervals (Day et al., 2001). The microdialysis probe has a diameter ranging from 200-500 μm resulting in a volume resolution of at least 1 $mm^3$ (Portas et al., 2000). Compounds in the samples are commonly separated on a High Performance Liquid Chromatography (HPLC) column, or less frequently, using Capillary Electrophoresis (CE) or capillary Liquid Chromatography (LC) columns (Kennedy et al., 2002). The molecules of interest are detected in the flow-through by analytical methods such as gas chromatography, radioenzymatic assay, radioimmunological measurement, fluorometry, electrochemical detection or mass spectrometry.

The main drawback of microdialysis is its temporal resolution, which can be several orders of magnitude lower than the time scale of electrical activity of brain cells. For example, the neurotransmitter acetylcholine (ACh) is presumably released in the cerebral cortex during short periods, e.g., 250 ms (McCormick et al., 1993). However, a typical microdialysis/HPLC system with femtomole detection limit can analyze a sample every 5-30 min (Day et al., 2001). If the microdialysate is analyzed via capillary electrophoresis combined with laser-induced fluorescence, nanoliter samples may be collected and the temporal resolution reduced to ~60 s (Lena et al., 2005). However, laser-induced fluorescence requires a method to conjugate a fluorophore to the analyte. Further, experimental results using capillary electrophoresis combined with fluorescence for most neurotransmitters, including ACh, have not been published to date. Detection of ACh by tandem mass spectrometry still requires several minutes per sample (Shackman et al., 2007; Zhang et al., 2007).

Temporal resolution of microdialysis systems can be improved at the expense of sensitivity, making detection of neuroactive substances problematic. To circumvent this problem, substances known to increase levels of neurotransmitters are included in the microdialysis perfusate (e.g., Himmelherber et al., 1998). In this respect, the practice of adding acetylcholine esterase inhibitors for ACh measurements is particularly controversial as the inhibitors perturb the physiology by artificially raising levels of ACh in the brain (Day et al., 2001).

Direct in vivo electrochemical methods rely on implanted electrodes measuring the redox current generated by the substances of interest at the electrodes. These techniques, referred to as amperometry, chronoamperometry and fast-scanning voltammetry, differ mostly in the stimulation waveform applied to the measuring electrode (Michael and Wightman, 1999).

Electrochemical methods have been used to detect, for instance, plasma glucose levels. In the brain, the most successful use of electrochemistry has been in the detection of dopamine, with a temporal resolution below one second (Robinson et al., 2003). Although detection of choline looks promising, electrochemical detection of ACh has proven difficult and current designs have a detection limit of 80 nM-660 nM (Mitchell, 2004; Bruno et al., 2006) in vitro, whereas estimates of basal levels using microdialysis are on the order of 4 to 100 nM (e.g. Rasmusson et al., 1992; Jimenez-Capdeville and Dykes, 1996; Himmelheber et al., 1998).

The main drawback of electrochemical methods is the lack of chemical sensitivity (Michael and Wightman, 1999). Electrochemical methods are, for instance, unable to differentiate between norepinephrine and dopamine (Robinson et al., 2003). Selectivity can be enhanced by coating electrodes, but at the expense of temporal resolution. Furthermore, electrochemical measurements are often contaminated by signals from precursors or metabolites of neurotransmitters, or unrelated compounds. For instance serotonin electrodes detect two metabolites of serotonin, 5-hydroxyindolacetic acid and uric acid (Cespuglio et al., 1998; Nakazato and Akiyama, 1999).

The difficulty in measuring single biochemical molecules in-vivo is even greater when multiple molecules need to be specifically detected simultaneously at the same site. Studies using voltammetry demonstrated the possibility to record several substances at the same electrode, but with the same selectivity shortcomings as described above (e.g., Nakazato and Akiyama, 1999). As such, neither microdialysis nor electrochemical techniques are adequate to measure simultaneously and unambiguously two biochemicals.

A recent approach, called FLIPE (Fluorescent indicator protein for glutamate), uses a genetically engineered chimeric protein composed of a glutamate binding site flanked by a blue and a yellow fluorescent protein (Okumoto et al., 2005). Following cell surface expression of the FLIPE sensor, binding of glutamate to the protein elicits a conformational change leading to a Fluorescence Resonance Energy Transfer (FRET) from the blue to the yellow fluorophore, which can be optically detected.

The main drawback of this method is its lack of flexibility, since it entails (1) finding a natural binding protein for the molecule of interest, from which the binding site is derived (2) modifying the chimera to provide enough molecular motion for FRET to occur, a step that requires extensive mutagenesis and screening, and (3) expressing the FLIPE sensor in the cells of interest in the brain.

Accordingly, the need remains for a method for a sensitive and specific in vivo detection of neurotransmitters with good temporal resolution.

SUMMARY OF THE INVENTION

A method is provided for measuring neuroactive substances in live brain using optical detection. According to an exemplary embodiment of the present invention, the method for measuring neurotransmitters in vivo comprises the steps of producing cellular sensors, called neurofluocytes, that emit an optical signal when detecting specific biochemical signalling molecules such as neurotransmitters or neuromodulators; implanting the cellular sensors into live tissue; and detecting the optical signal using microscopy techniques optimized for deep tissue imaging.

In one aspect of the invention, a method for in vivo detection of a biochemical substance in an animal comprises culturing neurofluocytes that stably express a receptor of the biochemical substances by transfecting cells with cDNA of the receptor and a tag that will emit a detectable energy in the presence of the biochemical substance, implanting the neurofluocyte into the animal's brain; and detecting the energy emission of the tag. In a first embodiment, the biochemical substance is a neurotransmitter, the tag is a fluorophore, and the step of detecting includes forming an opening in the animal's skull and optically detecting fluorescent emissions using a two-photon laser scanning microscope. In an alternative embodiment, the tag is an optical reporter protein. Multiple biochemical substances can be simultaneously detected by culturing neurofluocytes that express different receptors and have different fluorescent tags that produce optical signals at distinguishable wavelengths.

The inventive method would be useful to both basic science laboratories, to help discover how biochemical compounds are released in the normal and diseased body, and pharmaceutical companies. For example, with regard to the brain, the inventive method will help pharmaceutical companies discover novel neurological or neuropsychiatric drugs in preclinical live animal studies. The superior specificity and temporal resolution of our technique can be used to establish the biochemical effects of new compounds and to decide if they should proceed in the drug development pipeline.

The demonstrated ability of the inventive method to detect release of cortical acetylcholine is especially suitable to developing cholinergic therapies in animal models of Alzheimer's disease.

The present invention provides a method for detecting biochemical substances in the live brain. The method relies on recombinant expression of receptors in a fluorescent-based cell assay system, a technology used in fluorescent imaging plate reader, which is known in the art (FLIPR, Lang et al., 2006), but provides a novel method involving that use transplanted, light-emitting cultured cells to detect neurotransmitters or neuromodulators in the brain of live animal.

In one implementation of the inventive method, the fluorescent cell-based assay, routinely employed in high-throughput screening to test many different ligands against a single receptor, is used to create implantable neurofluocytes that can detect a single endogenous neurotransmitter in rat neocortex. The state of each cell is imaged with in vivo two-photon laser scanning microscopy (TPLSM). In another implementation, HEK293 cells were transfected with the $Ca^{2+}$-coupled M1 muscarinic receptor and the genetically encoded FRET-based $Ca^{2+}$ biosensor TN-XXL. In the presence of acetylcholine (ACh), a M1-mediated $Ca^{2+}$ increase is transduced by TN-XXL into a FRET-based optical signal. In vitro, FRET-based signals in individual neurofluoctes could be detected at a concentration of ~10 nM ACh (~30% change in 7 s) and increased monotonically toward a saturation level of ~1 μM ACh (>90% change in 5 s).

Neurofluocytes were implanted in rat neocortex to a depth of several hundreds of micrometers and imaged by TPLSM. In control studies, ejection of 4 to 40 nl ACh (1 mM) near the neurofluocytes induced a 15% signal change (6 trials, ~50 cells/trial, 2 rats), while sham ejections led to no discernable change. Implanted cells had normal morphology and responded for at least 6 hrs. Endogenous release of ACh was generated by electrical stimulation of nucleus basalis magnocellularis (NBM) and verified by desynchronization of the electrocorticogram. Each NBM stimulation triggered up to a 30% signal change in ~5 s, presumably due to ACh release near the neurofluocytes.

The modularity of the inventive technique allows for the realization of different receptor/sensor pairs as a means for detection of other neurochemicals, including neuropeptides. The only requirement is that the molecule induces a change in an optically-reportable signal, e.g., $Ca^{2+}$, cAMP, or protein kinase A activity, inside the neurofluocytes. Lastly, chronic studies may require isogeneic cell lines, as used in ex vivo gene therapy.

BRIEF DESCRIPTION OF THE DRAWINGS

FIG. 1*b* illustrates an exemplary experimental set-up for monitoring optical signals in an animal.

FIG. 3*a* shows the response (fractional fluorescence change) to a puff of ACh through an extracellular electrode and FIG. 3*b* shows the response to electrical stimulation of NBM.

DETAILED DESCRIPTION OF THE INVENTION

The inventive method relies on genetically engineered cells, called neurofluocytes, that are designed to emit a fluorescence signal when detecting a specific neuronal signaling molecule. Neurofluocytes express a membrane receptor acting on an intracellular messenger such as calcium or cyclic AMP upon binding the molecule of interest, and a protein that emits light depending on the amount of the intracellular messenger. Alternatively, if the receptor induces a membrane potential change, voltage-sensitive dyes can be used to report on the activation of the receptor. Neurofluocytes are subsequently implanted in-vivo. The fluorescence signal from these cells is detected, for example, by two-photon laser scanning microscopy.

Figure 1A:
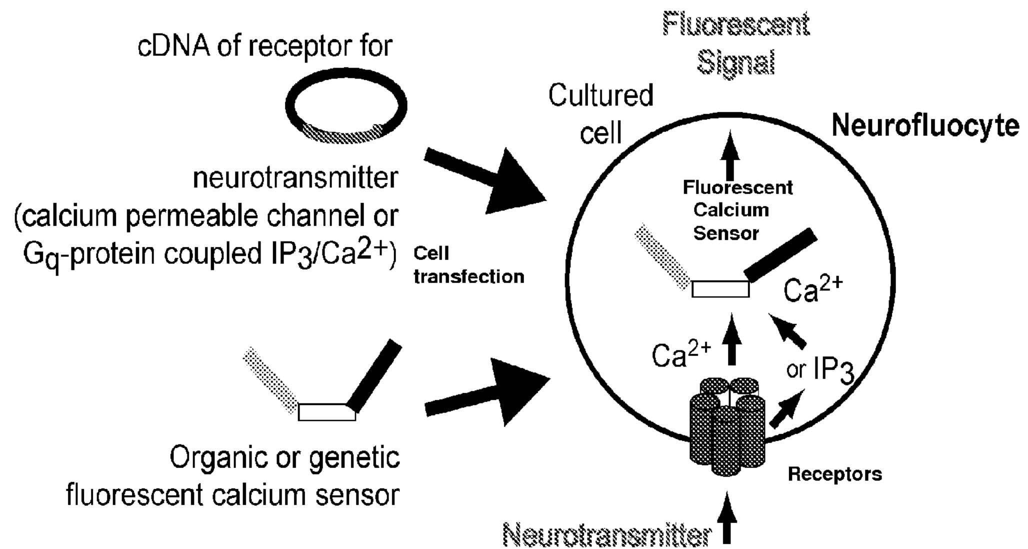
FIGS. 1*a* and 1*b* are diagrams showing the principle of the inventive method to detect a neurotransmitter in live brain tissue, where FIG. 1*a* provides an example of a neurofluocyte that expresses receptors for intracellular calcium and includes a fluorescent calcium indicator.
Figure 1B:
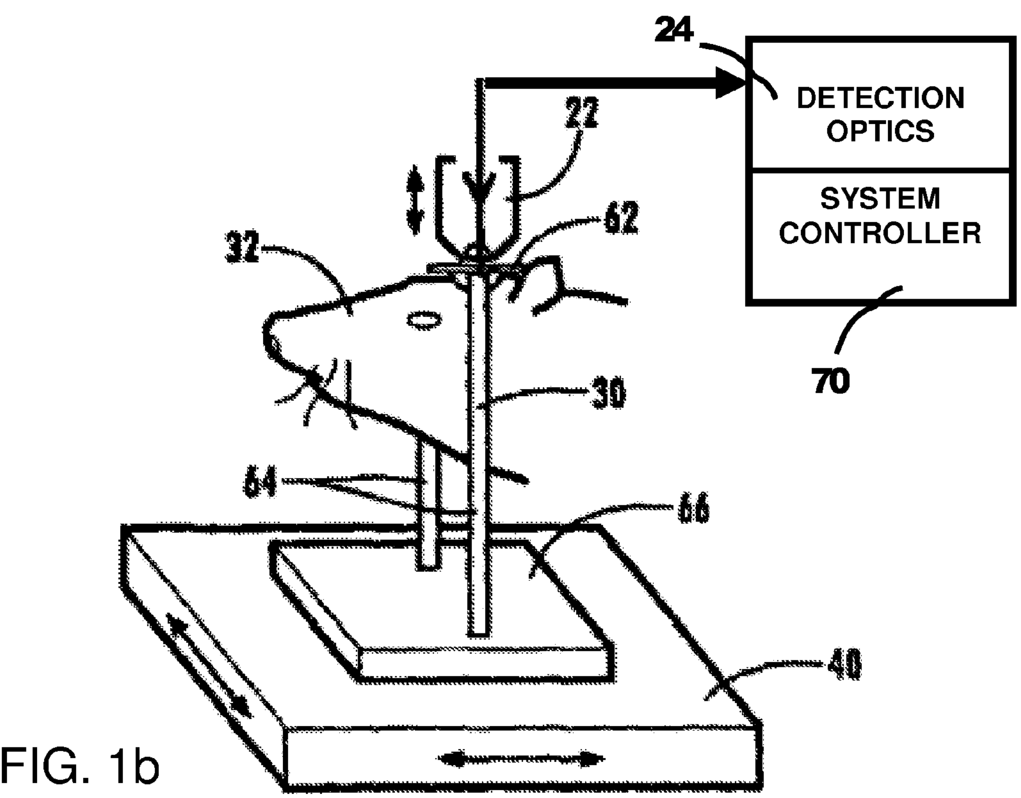

FIGS. 1*a* and 1*b* illustrate the principle of the inventive method to detect a neurotransmitter in live brain tissue. FIG. 1*a* is a diagram showing a cultured cell that has been stably co-transfected with eukaryotic expression vectors containing cDNA that encode receptors for the targeted neurotransmitter, in this example, intracellular calcium, and a fluorescent calcium indicator. The resulting neurofluocyte is injected into the live brain of a model animal, which, in this case, is a rat.

FIG. 1*b* shows the basic apparatus for optical examination of the live brain to observe and measure the expression of neurotransmitter using two-photon laser scanning microscopy (TPLSM). The detection optics 24 include a combination of mirrors, filters, lenses and detectors which receive the photons from the animal preparation 32 through the objective lens 22. A digital image acquisition and storage system 70 is provided to store sections in the form of digital images. Such a system 70 comprises a computer system and suitable acquisition software and imaging software to visualize the animal preparation (rat brain). Additional software and/or hardware can be included to provide positioning control and coordination of the translation stage 40, allowing precise positioning and assignment of reference coordinates to the stored images. An optically transparent cranial window, such as a coverslip, may be placed over the opening created by the craniotomy.

The head-fixed mount 30 is constructed from a metal plate 62 which is directly attached to the animal preparation 32. The metal plate 62 is mounted onto metal rods 64 which attach to a kinematic baseplate 66 that can be removed and replaced with high precision. The kinematic base plate 66 attaches to a translation stage 40 that can be connected to system controller 70 to provide computer control to deliver micrometer position accuracy. Such a system is disclosed in U.S. Pat. No. 7,258,687, which is incorporated herein by reference.

Additional details of the components of the TPLSM and methods of in vivo brain imaging are provided in Chapter 6 ("Principles, Design and Construction of a Two-Photon Laser-Scanning Microscope for In Vitro and In Vivo Brain Imaging", by P. S. Tsai, et al.) of *In Vivo Optical Imaging of Brain Function*, ed. Ron D. Frostig, 2002, CRC Press, pp. 113-171, which is incorporated herein by reference.

The inventive technique can be applied to acute experiments in anesthetized animals, during which cells are imaged a few hours after injection. The same methodology can be extended to chronic studies in awake behaving animals, during which biochemical monitoring can take place several days after the implantation procedure and could last for weeks. Finally, genetically engineered animals can be produced that naturally express the neurofluocytes, for example, in endogenous fibroblasts expressing a receptor of interest and appropriate sensor for an intracellular messenger. The inventive method is not only applicable to monitor neurotransmitter receptors in the brain but is also relevant to detect bioactive molecules in other organs.

Neurofluocytes are produced from convenient, easy to procure expression systems such as Human Embryonic Kidney cells (e.g., HEK293). This type of cell is suitable for acute experiments lasting less than a day.

In chronic studies that could extend over several months, cells originating from the strain of the animal later to be used (e.g., an isogeneic cell line) can be used to prevent an immunological reaction to the graft. The concept of implanting genetically-modified cells, known as ex vivo gene therapy, into the CNS to supplement function (Gage et al., 1987) has led to a large body of work describing various donor cells, methods of gene transfer and subsequent tests of persistent gene expression and histological effects of chronic implantation (Kawaja and Gage, 1992). A number of cell types have been used, including primary and immortalized fibroblasts, glial cells, peripheral neural tissue, and tumor-derived cells (Kawaja and Gage, 1992; Snyder and Senut, 1997; Pizzo et al., 2004). Autologous cells can be readily created from Schwann cells, endothelial cells and astrocytes. Of particular interest are skin fibroblasts, which are easy to harvest, maintain and made to express exogenous proteins that can promote regeneration, rescue and recovery of damaged neural tissue (Tuszynski et al., 1994; Grill et al., 1997; Liu et al., 1999). More importantly, rat skin fibroblasts that have been implanted into the rat brain can survive for several months, exhibit contact inhibition and, thus, intercalate into the surrounding neuropil without growing into a mass (Kawaja and Gage, 1992). These cells can provide persistant expression of the transgenes for at least a year (Pizzo et al., 2004). Isogeneic grafts from inbred strains (Fischer 344) allows for cells to be harvested from a single animal, transfected, then implanted into many animals with results similar to autologous grafts, surviving at least 24 months (Kawaja and Gage, 1992). A significant obstacle encountered in past work has been the formation of a glial scar that may impede the free diffusion of neurotransmitters around the implanted cells (Kawaja and Gage, 1992). It may be possible to reduce this effect with the use of immune-suppressing drugs.

According to the present invention, host cells, such as HEK293 or fibroblasts, are cotransfected with the cDNAs of a membrane receptor for the molecule to detect and, in some embodiments, a fluorescent reporting protein. Such cDNAs are easily obtained either from academic laboratories or from commercial suppliers. To ensure consistent levels of receptor and probe (tag) in neurofluocytes, these cells are made to stably express the detector and reporter proteins using standard selection protocols after transient transfection. A less tedious and time-consuming procedure to produce stable neurofluocyte lines uses retroviral transfer of genetic material. This method has been generally accepted as the preferred means of creating cell lines with stable expression when cells exhibit stable growth and replication (Kawaja and Gage, 1992; Snyder and Senut, 1997). Replication-incompetent recombinant lentiviruses provide an efficient way to incorporate large transgenes into the genome of host cells.

Finally, genetically engineered animals can be produced that naturally express the neurofluocytes, for example, in endogenous fibroblasts expressing a receptor of interest and appropriate sensor for an intracellular messenger.

Overall, the methods involved to develop neurofluocytes for various neuroactive substances are standard cellular/molecular biology procedures. The inventive method's adaptability constitutes a major advantage over prior art methods.

The membrane receptors can include all G-protein coupled receptors linked to the $IP_3/Ca^{2+}$ or other second messenger pathways, allowing the detection of a wide variety of compounds that includes virtually all neurotransmitters or neuropeptides. In addition, ionotropic receptors endowed with a large calcium permeability such as the nicotinic $\alpha_7$, 5-$HT_{3A}$, the purinergic $P_{2x}$ and the $GluR_3$ subunits can be used as initial sensors for acetylcholine, serotonin, ATP or glutamate, respectively. Further gain of function could be obtained by expressing artificially mutated receptors that would optimize the optical signal of neurofluocytes (e.g., by increasing calcium permeability). The sensitivity of receptors to their natural agonist and their usual insensitivity to metabolites or precursors provide significant advantages over prior art methods.

In an exemplary embodiment of the invention, activation of receptors is reported by a fluorescent organic dye or by an optical reporter protein.

Fluorescent organic dye. Receptors that increase intracellular calcium can be paired with calcium-sensitive fluorescent dyes. These organic compounds, such as Calcium Green or Oregon Green-BAPTA can be easily introduced into the cultured cells using their acetoxymethyl (AM) derivatives (Grynkiewicz et al., 1985). These molecules allow robust detection of activation of $Ca^{2+}$ influx triggered by activation of $G_q$-protein coupled $IP_3/Ca^{2+}$ second messenger system or via the opening of calcium-permeable channels. In addition, these indicators are well-suited for two-photon microscopy (Denk et al., 1990; Svoboda and Yasuda, 2006). However, long-term experiments (>1 day) with these dyes are not possible due to their eventual sequestration into intracellular organelles and/or degradation. If activation of the receptors results in a change in membrane potential, organic voltage-sensitive fluorescent dyes can be used as well. For instance, Huang et al. (2006) demonstrated the usefulness of using a combination of these dyes in transfected HEK293 cells to obtain a large and fast FRET (Fluorescence Resonance Energy Transfer) signal in response to cell depolarization.

Optical reporter protein. Another possibility is to cotransfect the sensor cells with an optical reporter protein. In principle, possible reporters would include bioluminescent proteins such as aequorin, however, for imaging reasons described below, fluorescent probes are preferred. These can be any of the several fluorescent genetically engineered calcium indicators already available, including calmodulin-based [$Ca^{2+}$] sensors such as Yellow Cameleon 3.60 and 3.12, Camgaroo 2, Inverse pericam, G-CaMP, G-CaMP2, and troponin C-based [$Ca^{2+}$] sensor (TN-L15) (see Kleinfeld and Griesbeck, 2005). Among fluorescent reporting proteins, those based on Fluorescence Resonance Energy Transfer (FRET) are particularly valuable since the differential change in the FRET signal allows one to distinguish between artificial variations in fluorescence intensity, such as those induced by animal motion, and bona fide signals.

An example of such FRET probe is TN-XXL (for extra-extra large). This high performance probe is the latest member of the troponin C-based family calcium indicators (Mank et al., 2008; Heim and Griesbeck, 2004; Mank et al., 2006) and consists of a troponin-C $Ca^{2+}$ binding site flanked by enhanced cyan fluorescent protein (eCFP) and yellow fluorescent protein (eYFP). Upon calcium binding, troponin-C undergoes a conformational change that triggers FRET between the two fluorophores. An increase in intracellular $Ca^{2+}$ leads to a characteristic decrease in CFP fluorescence and an increase in YFP fluorescence. Using the same principle, receptors that stimulate a second messenger system other than the $IP_3/Ca^{2+}$ pathway can still activate a calcium indicator. This can be achieved by coexpressing in neurofluocytes either the promiscuous G-protein $G_{\alpha 16}$ or a G-protein chimera capable of coupling the receptor with the $IP_3/Ca^{2+}$ pathway (Coward et al., 1999). Alternatively, receptors that modulate intracellular cAMP levels via $G_{i/0}$ or $G_s$ G-proteins can be coupled with the genetically-encoded fluorescent probe AKAR (Zhang et al., 2005).

The temporal resolution of neurofluocytes is determined, to a large extent, by the kinetics of the light-emitting reporter. The measured decay time of organic dyes and fluorescent reporting proteins ranges from sub-second to seconds (e.g., Mank et al., 2006), which allows the inventive method to be faster than microdialysis/separation/detection techniques.

Neurofluocytes can be micro-injected in the brain of live animals or in other tissue of interest such as in vitro vertebrate brain slices. An exemplary procedure for implantation into the cerebral cortex of anesthetized rats involves loading neurofluocytes in a thin glass needle (shank diameter ~100 μm) fitted to a nanoliter injector. The pipette is lowered into the desired brain region through a craniotomy located using stereotaxic coordinates. Neurofluocytes are then delivered in 5 nl increments. After removal of the injection needle, the craniotomy is covered with an optical window. In case of acute experiments, the animal can be subsequently imaged for several hours. In chronic studies, the animal would be allowed to wake up from the surgery and recover from the cell implantation for a few days. Although gene expression has been shown to decrease over varying time-scales, in the short term of several weeks, expression of the receptors and light reporters should remain strong.

The spatial resolution of the inventive technique is determined by the size of the injection site, currently ~100 μm in diameter. Although this parameter is larger than the spatial resolution of non-enzyme assisted in vivo voltammetry (which depends mainly on the tip diameter of the recording electrode), it compares favorably with that of enzyme assisted voltammetry (Bruno et al., 2006) and the microdialysis/HPLC method (Day et al., 2005).

A key feature of the inventive method is the ability to detect several neurotransmitters/neuropeptides simultaneously in the same brain region. This can be achieved by injecting a mix of neurofluocytes designed to detect different molecules. To distinguish the different responses, each population of neurofluocytes can be "tagged" with a different fluorophore, the emission of which does not overlap with the functional signal. The tags include, but are not restricted to, a multitude of non-functional fluorescent organic dyes, fluorescent proteins or even quantum dots. In a similar fashion, tagged control cells, not expressing the receptor of interest but providing an optical signal, can be injected with neurofluocytes to assess the level of any endogenous response in the host cells.

Optical signals from neurofluocytes injected into brain tissue ex vivo such as in mammalian brain slices can be imaged easily using conventional brightfield fluorescence microscopy. Neurofluocytes implanted in the brain of a live animal can be recorded using well-established in vivo imaging techniques through the craniotomy used to implant the cells. These methods allow optical recording deep inside the brain of anesthetized or unanesthetized animals such as rats.

Optical recording of the whole implantation locus as a single point is possible. However, whole frame imaging techniques are more capable than single location photometric measurements to discriminate artifactual signals coming from dead cell debris, animal motions, etc. In addition, single-point measurements lack optical sectioning in the z–direction, preventing measurement of biochemicals at different depths in the tissue.

Imaging deep inside live tissue present challenges that have been solved by the advent of two-photon laser scanning microscopy (TPLSM) (see, e.g., U.S. Pat. No. 5,034,613 of Denk et al., which is incorporated herein by reference.) TPLSM allows full-frame imaging of implanted neurofluocytes at depths down to 500 μm from the surface of cerebral cortex of anesthetized rats. To image deeper inside the brain, and to record neurofluocytes in awake animals, several microscope techniques based on fiber optics have been described, which allow animals to behave relatively unconstrained. For instance, a miniaturized two-photon microscope setup affixed to the head of rats has been demonstrated (Helmchen et al., 2001). To allow neurotransmitter monitoring in subcortical structures that cannot be imaged directly by two-photon microscopy due to depth limitations, neurofluocytes can be visualized by minimally invasive one-photon or multi-photon endoscope-based techniques which allow imaging in locations such as striatum or hippocampus (e.g., Jung and Schnitzer, 2003; Jung et al., 2004; Levine et al., 2004).

Validation of the inventive technique was performed by producing and testing neurofluocytes designed to detect acetylcholine (ACh-neurofluocytes) in cerebral cortex.

Several types of neurofluocytes have been designed and produced:

ACh-neurofluocytes loaded with fluorescent organic dye. These ACh-neurofluocytes were devised by taking advantage of the intrinsic although highly variable expression of intrinsic acetylcholine muscarinic receptors in HEK293 cells (Taylor and Tsien, 2006). Populations of HEK293 cells were loaded with the cell-permeant organic indicator Ca-Green-1 AM prior to testing.

ACh-neurofluocytes expressing a muscarinic receptor and fluorescent protein. To enhance the response to acetylcholine and augment the fluorescence signal, a clonal cell line of ACh-neurofluocytes stably expressing the M1 muscarinic acetylcholine receptor (GenBank Accession No. NM_080773; SEQ ID NO. 1) and the TN-XXL genetic calcium probe was created. These cells are referred to here as M1-TN-XXL neuro-fluocytes. HEK-293 cells were transduced with lentiviruses modified to carry the M1 muscarinic acetylcholine receptor or the TN-XXL FRET intracellular calcium indicator as transgenes. Clonal cells were selected subsequently based on the highest response to acetylcholine in vitro.

Fibroblast-based neurofluocytes. In preliminary experiments, chemical transfection was used to establish that rat skin fibroblasts from Fisher 244 rats can express TN-XXL.

In addition, using lentiviral transduction, HEK293 cells stably expressing TN-XXL and the non-functional red fluorescent protein mCherry for tagging purposes were created as control neurofluocytes. Neurofluocytes designed to detect serotonin by transiently cotransfecting HEK cells with the cDNA of the calcium-permeable ionotropic receptor 5-$HT_{3A}$ (GenBank Accession No. NM_024394; SEQ ID NO. 2) and that of TN-XXL were also engineered. In vitro, these cells responded robustly to 3-10 μm serotonin applied in the bath. These experiments demonstrate the flexibility of the inventive method to design sensors for different neurotransmitters.

Figure 2A:
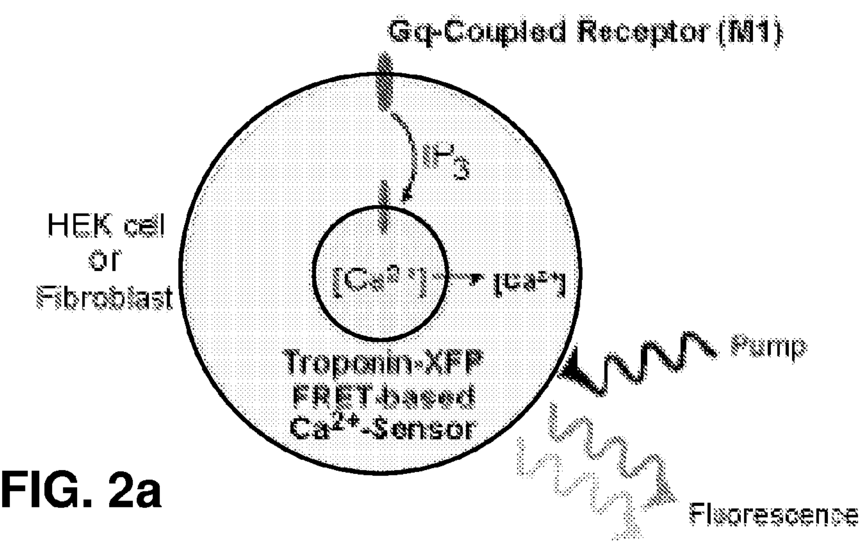
FIG. 2*a* provides a diagram of the detection mechanism and FIG. 2*b* illustrates the in vitro 2-photon FRET signals in M1-TN-XXL neurofluocytes in response to bath application of acetylcho line.
Figure 2B:
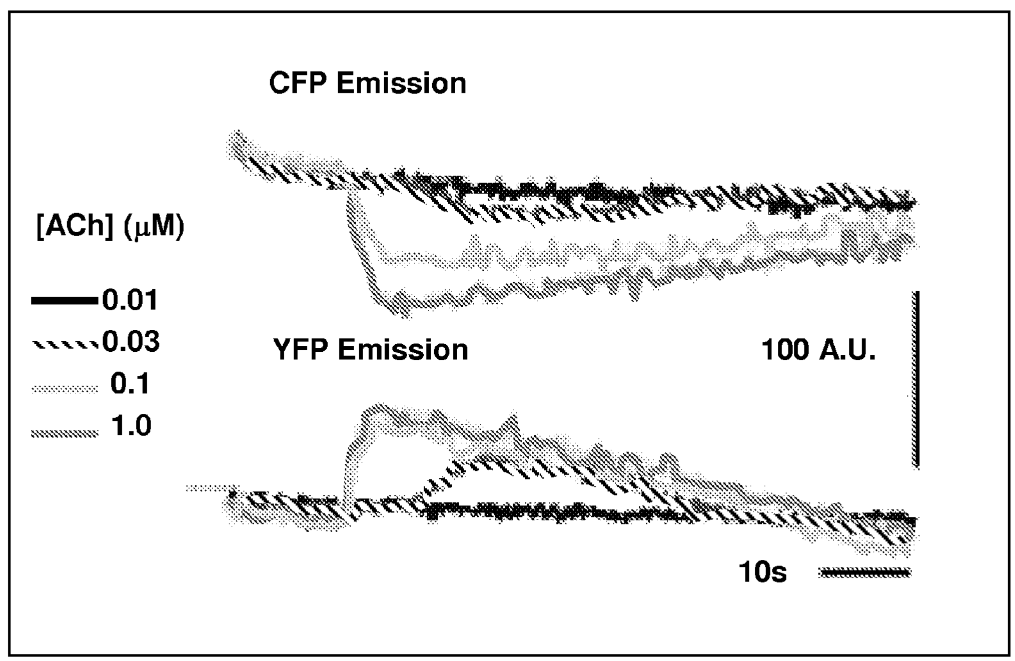

The sensitivity and specificity of ACh-neurofluocytes have been determined by in vitro testing:

M1-TN-XXL neurofluocytes. ACh-neurofluocytes were tested in vitro for their sensitivity to acetylcholine. Application of ACh (10 nM to 10 μM) via bath perfusion elicited robust FRET responses in ACh-neurofluocytes imaged by two-photon microscopy, with a 10 nM detection threshold. In addition, ACh-neurofluocytes are insensitive to norepinephrine, serotonin, GABA, glutamate, glycine, aspartate+glycine and dopamine. FIG. 2*a* provides a diagram of the detection mechanism. FIG. 2*b* illustrates the in vitro 2-photon FRET signals in M1-TN-XXL neurofluocytes in response to bath application of acetylcholine of 10 nM, 30 nM, 1 μM and 10 μM of ACh.

ACh-neurofluocytes loaded with fluorescent organic dye. ACh-neurofluocytes were tested in vivo to assess their ability to detect acetylcholine applied externally or released in cerebral cortex by a neural mechanism. HEK293 cells loaded with Ca-Green-1 were injected into the parietal cortex of anesthetized rat to depth of 300 μm below the pial surface. Depending on the injection volume, tens of cells can be visualized simultaneously in the same field of view using in vivo TPLSM. Cell morphology was normal, with no sign of degradation after several hours. Implanted cells did not drift from the field of view, which indicates that brain tissue provides adequate support for neurofluocytes. Periodic cell motions from heart beat and respiration were limited to 2 to 3 μm displacements.

Figure 3A:
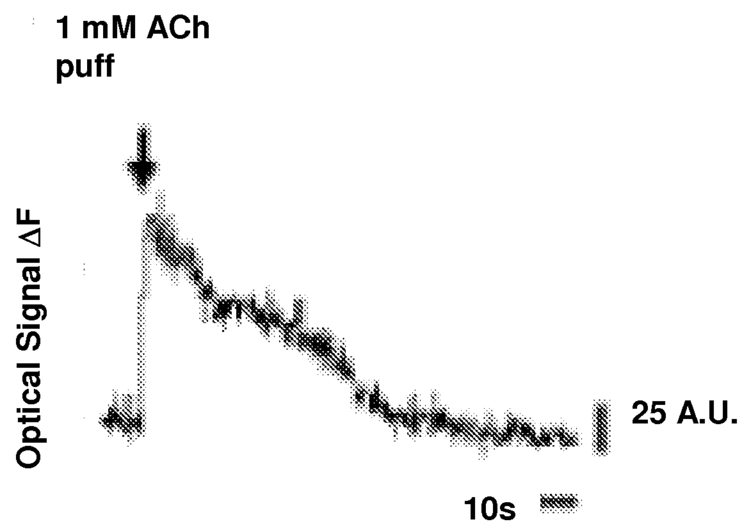
FIGS. 3*a* and 3*b* illustrate the response of HEK cells, loaded with Ca-Green-1 that were implanted 200 μm below the pial surface and imaged with TPLSM, where

To test in vivo sensitivity, a pipette containing 1 mM ACh fitted to a nanoliter injector was placed close to the injection site. Ejection of 20 nl of ACh elicited a large fluorescent transient in neurofluocytes (FIG. 3*a*). This result establishes that ACh-neurofluocytes can respond one or two orders of magnitude faster than microdialysis.

Figure 3B:
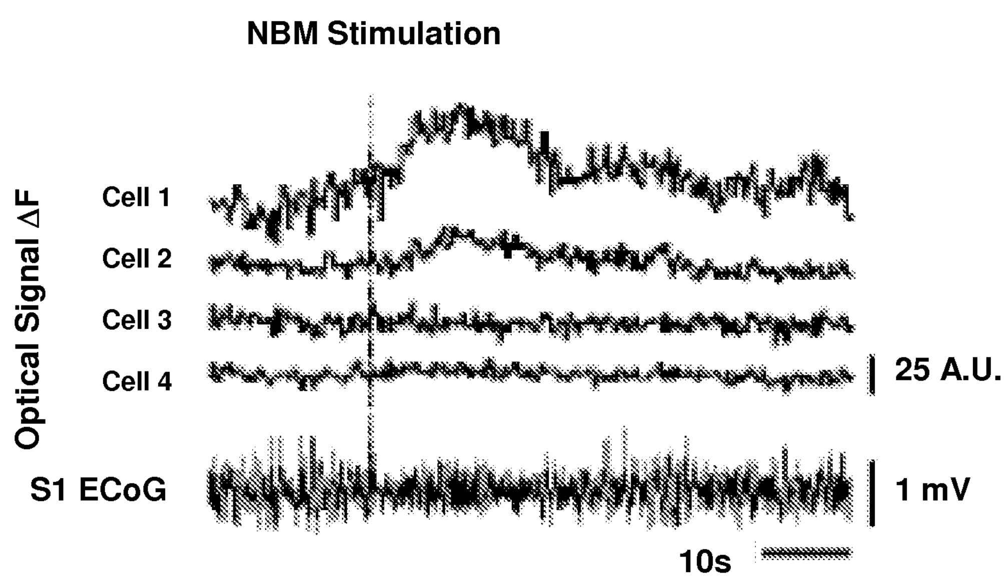

Electrical activation of the cholinergic input to cerebral cortex provides a test-bed to validate the ability of ACh-neurofluocytes to detect physiologically relevant amounts of ACh. The cerebral cortex is massively innervated by cholinergic fibers (Mechawar et al., 2000) that come from neurons in the basal forebrain. In particular, in rat, the NBM (Nucleus Basalis Magnocellularis), medial septal nucleus, and the diagonal band of Broca extend cholinergic projections to the neocortical mantle and play a critical role in cortical activation (Metherate et al., 1988; McCormick, 1993). In rats anesthetized with urethane, electrical stimulation of the NBM results in a characteristic transition of the electrocorticogram (ECoG) from large amplitude, slow wave potentials to low amplitude, higher frequency electrical signals (Metherate et al., 1992; Metherate and Ashe, 1992). This phenomenon, called desynchronization, is directly related to increased levels of cortical ACh (Metherate et al., 1992). Cortical desynchronization is therefore the hallmark of ACh release in cortex in either the anesthetized or awake animal (Bakin and Weinberger, 1996). Urethane-anesthetized rats were injected with HEK293 cells loaded with Calcium Green in the cerebral cortex and a bipolar stimulating electrode was implanted in NBM together with ECoG-recording electrodes to detect desynchronization in cerebral cortex upon NBM stimulation. Electrical stimulation of the NBM led to a robust, repeatable, ~10 s epochs of desynchronization. Some, but not all, implanted cells simultaneously imaged with TPLSM gave a functional $Ca^{2+}$ signal, consistent with the uneven expression of endogenous muscarinic receptors in HEK293 cells (FIG. 3*b*).

Figure 4:
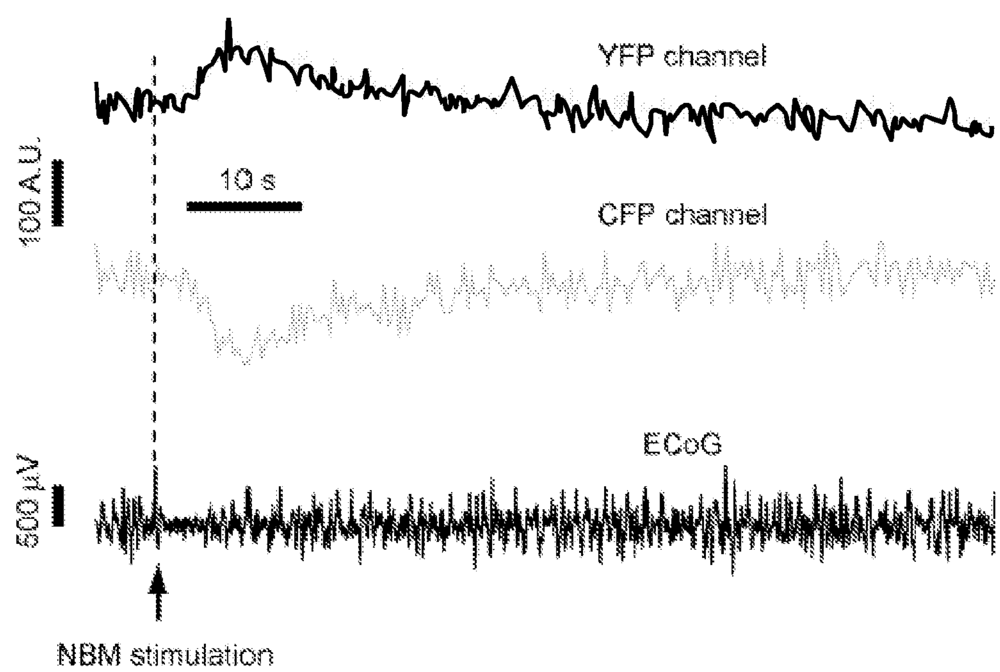
FIG. 4 illustrates the response of M1-TN-XXL neurofluocytes implanted in the cerebral cortex of a rat to NBM stimulation.

M1-TN-XXL ACh-neurofluocytes. A similar set of experiments was conducted with stably transfected M1-TN-XXL neurofluocytes. In addition to response to injections of ACh, these ACh neurofluocytes gave a robust FRET signal upon single NBM stimulation and concomitant ECoG desynchronization. FIG. 4 illustrates the signals generated during detection of M1-TN-XXL neurofluocytes implanted in the cerebral cortex of a rat subjected to NBM stimulation.

Overall, in vivo validation experiments demonstrated that the inventive method is superior than microdialysis/separation/detection and electrochemical techniques. The inventive method can unambiguously detect single trial output of acetylcholine in cortex, with a temporal resolution in seconds, without addition of acetylcholinesterase inhibitors and without background signals from other compounds or endogenous cellular activity, as evidenced by the lack of FRET signal before the NBM stimulation. It was also demonstrated that neurofluocytes can remain functional up to six days after their implantation in the brain. Furthermore, responses of neurofluocytes to NBM stimulation is abolished by intracerebral injection of atropine, the canonical antagonist of muscarinic receptors.

Simultaneous in vivo imaging of different neurofluocytes can be performed to provide two separate measurements of the same target neuronal signaling molecule or to detect two different signaling molecules. This capability was demonstrated by in vivo imaging of M1-TNN-XXL ACh-neurofluocytes and HEK293 cells stably expressing TN-XXL and mCherry. Testing also verified that electrical stimulation of the NBM elicits a FRET response only in M1-expressing cells, but not in control cells that express mCherry.

A clonal line of neurofluocytes is being created for serotonin (5-HT-neurofluocytes) to stably express the 5-HT3A receptor and the calcium reporter TN-XXL. By co-injecting 5-HT- and ACh-neurofluocytes, simultaneous measurement of serotonin and acetylcholine in the cerebral cortex of anesthetized rats can be demonstrated. In addition, lines of fibroblast-based ACh- and glutamate neurofluocytes can be created for long term implantation and recording in rat cortex.

The inventive method has several major advantages over existing art, including 1) better temporal resolution than conventional microdialysis/HPLC techniques by one to two orders of magnitude; 2) increased sensitivity compared to all other methods, capable of detecting single-trial output of cortical acetylcholine with good signal-to-noise ratio without addition of acetylcholinesterase inhibitors, a level of sensitivity never reached until now in vivo; 3) higher specificity than in vivo electrochemical methods—the inventive sensors are virtually insensitive to precursors or metabolites of the neuroactive substance they are designed to detect; 4) simultaneous detection of multiple compounds—many types of neurotransmitters or neuromodulators can be released synchronously at the same location. Because these compounds are often chemically unrelated, simultaneous detection using conventional methods remains difficult; 5) versatility—many biochemical substances present in tissue at low nanomolar concentrations, such as neuropeptides, are difficult to monitor in vivo by current methods due to lack of a specific and sensitive detection assay. In contrast, by using cloned cDNAs coding for neurotransmitter or neuromodulator receptors as primary sensors, the inventive method can be rapidly adapted to design, test, implant and record probes for a wide variety of biochemical substances using the same methodology.

The following references are incorporated herein by reference.

Bakin, J. S. and Weinberger, N. M. (1996) Induction of a physiological memory in the cerebral cortex by stimulation of the nucleus basalis. *Proc. Natl. Acad. Sci. U.S.A.* 93, 11219-11224.

Bruno, J. P., Gash, C., Martin, B., Zmarowski, A., Pomerleau, F., Burmeister, J., Huettl, P. and Gerhardt, G. A. (2006) Second-by-second measurement of acetylcholine release in prefrontal cortex. *Eur. J. Neuroscience* 24, 2749-2757.

Coward, P., Chan, S. D., Wada, H. G., Humphries, G. M. and Conklin, B. R. (1999) Chimeric G proteins allow a high-throughput signaling assay of Gi-coupled receptors. *Anal Biochem.* 270, 242-248.

Cespuglio, R., Burlet, S. and Faradj-Prevautel, H. (1998) 5-Hydroxyindoles compounds and nitric oxide voltammetric detection in the rat brain: changes occurring throughout the sleep-wake cycle. *J. Neural Transm.* 105, 205-215.

Day, J. C., Kornecook, T. J. and Quirion, R. (2001) Application of in vivo microdialysis to the study of cholinergic systems. *Methods* 23, 21-39.

Denk, W., Strickler, J. H., and Webb, W. W. (1990) Two-photon laser scanning microscopy. *Science* 248, 73-76.

Fillenz, M. (2005) In vivo neurochemical monitoring and the study of behaviour. *Neuroscience and Biobehavioral Reviews* 20, 949-962.

Gage, F. H., Wolff, J. A., Rosenberg, M. B., Xu, L., Yee, J. K., Shults, C. and Friedmann, T. (1987) Grafting genetically modified cells to the brain: possibilities for the future. *Neurosci* 23, 795-807.

Grill, R., Murai, K., Blesch, A., Gage, F. H., and Tuszynski, M. H. (1997) Cellular delivery of neurotrophin-3 promotes corticospinal axonal growth and partial functional recovery after spinal cord injury, *J. Neurosci.* 17, 5560-5572.

Grynkiewicz, G., Poenie, M., and Tsien, R. Y. (1985) A new generation of Ca2+ indicators with greatly improved fluorescence properties. *J. Biol. Chem.* 260, 3440-3450.

Heim, N. and Griesbeck, O. (2004) Genetically encoded indicators of cellular calcium dynamics based on troponin C and green fluorescent protein. J. Biol. Chem. 279, 14280-14286.

Helmchen, F., Fee, M. S., Tank, D. W., Denk, W. (2001) A miniature head-mounted two-photon microscope. high-resolution brain imaging in freely moving animals. *Neuron* 31, 903-912.

Himmelheber, A. M., Fadel, J., Sarter, M. and Bruno, J. P. (1998) Effects of local cholinesterase inhibition on acetylcholine release assessed simultaneously in prefrontal and frontoparietal cortex. *Neurosci.* 86, 949-957.

Huang, C. J., Harootunian, A., Maher, M. P., Quan, C., Raj, C. D., McCormack, K., Numann, R., Negulescu, P. A., Gonzalez, J. E. (2006) Characterization of voltage-gated sodium-channel blockers by electrical stimulation and fluorescence detection of membrane potential. *Nat. Biotechnol.* 24, 439-446.

Jimenez-Capdeville, M. E. and Dykes, R. W. (1996) Changes in cortical acetylcholine release in the rat during day and night: Differences between motor and sensory areas. *Neurosci.* 71, 567-579.

Jung, J. C. and Schnitzer, M. J. (2003) Multiphoton endoscopy. *Opt. Lett.* 28, 902-904.

Jung, J. C., Mehta, A., Aksay, E., Stepnoski, R. and Schnitzer, M. J. (2004) In vivo mammalian brain imaging using one- and two-photon fluorescence microendoscopy. *J. Neurophysiol.* 92, 3121-3133.

Kawaja, M. D. and Gage, F. H. (1992) Morphological and neurochemical features of cultured primary skin fibroblasts of Fischer 344 rats following striatal implantation, *J. Comp. Neurol.* 317, 102-116.

Kennedy, R. T., Watson, C. J., Haskins, W. E., Powell, D. H. and Strecker, R. E. (2002) In vivo neurochemical monitoring by microdialysis and capillary separations. *Current Opinion in Chemical Biology* 6, 659-665.

Kleinfeld, D. and Griesbeck, O. (2005) From art to engineering? The rise of in vivo mammalian electrophysiology via genetically targeted labeling and non-linear imaging. *PloS Biology* 3, 1685-1689.

Lang, P., Yeow, K., Nichols, A., and Scheer, A. (2006) Cellular imaging in drug discovery. *Nature Rev. Drug Discovery* 5, 343-356.

Lena, I., Parrot, S., Deschaux, O., Muffat-Joly, S., Sauvinet, V., Renaud, B., Suaud-Chagny, M. F. and Gottesmann, C. (2005) Variations in extracellular levels of dopamine, noradrenaline, glutamate, and aspartate across the sleep-wake cycle in the medial prefrontal cortex and nucleus accumbens of freely moving rats. *J. Neurosci. Res.* 81, 891-899.

Levine, M. J., Dombeck, D. A., Kasischke, K. A., Molloy, R. P. and Webb, W. W. (2004) In vivo multiphoton microscopy of deep brain tissue. *J. Neurophysiol.* 91, 1908-1912.

Liu, Y., Kim, D., Nimes, B. T., Chow, S. Y., Schallert, T., Murray, M., Tessler, A. and Fischer, I. (1999) Transplants of fibroblasts genetically modified to express BDNF promote regeneration of adult rat rubrospinal axons and recovery of forelimb function. *J. Neurosci.* 19, 4370-4387.

McCormick, D. A. (1993) Actions of acetylcholine in the cerebral cortex and thalamus and implications for function. *Prog. Brain Res* 98, 303-308.

Mank, M., Santos, A. F., Direnberger, S., Mrsic-Flogel, T. D., Hofer, S. B., Stein, V., Hendel, T., Reiff, D. F., Levelt, C., Borst, A., Bonhoeffer, T., Hübener, M. and Griesbeck, O. (2008) A genetically encoded calcium indicator for chronic in vivo two-photon imaging. *Nature Methods* 2008 Aug. 10.

Mank, M., Reiff, D. F., Heim, N., Friedrich, M. W., Borst, A. and Griesbeck, O. (2006) A FRET-based calcium biosensor with fast signal kinetics and high fluorescence change. *Biophys. J.* 90, 1790-1796.

Mechawar, N., Cozzari, C., and Descarries, L. (2000) Cholinergic innervation in adult rat cerebral cortex: A quantitative immunocytochemical description. *J. Comp. Neurol.* 428, 305-318.

Metherate, R., Tremblay, N. and Dykes, R. W. (1988) The effect of acetylcholine on response properties of cat somatosensory cortical neurons. *J. Neurophysiol.* 59, 1231-1352.

Metherate, R., Cox, C. L., and Ashe J. H. (1992) Cellular bases of neocortical activation: Modulation of neural oscillations by the nucleus basalis and endogenous acetylcholine. *J. Neurosci.* 12, 4701-4711.

Metherate, R. and Ashe J. H. (1993) Ionic flux contributions to neocortical slow waves and nucleus basalis-mediated activation: Whole-cell recordings in vivo. *J. Neurosci.* 12, 5312-5323.

Michael, D. J. and Wightman, R. M. (1999) Electrochemical monitoring of biogenic amine neurotransmission in real time. *J. Pharmaceu. Biomed. Anal.* 19, 33-46.

Mitchell, K. M. (2004) Acetylcholine and choline amperometric enzyme sensors characterized in vitro and in vivo. *Anal Chem.* 76, 1098-1106.

Nakazato, T. and Akiyama, A. (1999) High-speed voltammetry: dual measurement of dopamine and serotonin. *J. Neurosci. Methods* 89, 105-110.

Okumoto, S., Looger, L. L., Micheva, K. D., Reimer, R. J., Smith, S. J. and Frommer, W. B. (2005) Detection of glutamate release from neurons by genetically encoded surface-displayed FRET nanosensors. *Proc. Natl. Acad. Sci. U.S.A.* 102, 8740-8745.

Parikh, V., Pomerleau, F., Huettl, P., Gerhardt, G. A., Sarter, M. and Bruno, J. P. (2004) Rapid assessment of in vivo cholinergic transmission by amperometric detection of changes in extracellular choline levels. *Eur. J. Neurosci.* 20, 1545-1554.

Pizzo, D., Paban, V., Coufal, N. G., Gage, F. H., and Thal, L. J. (2004) Long-term production of choline acetyltransferase in the CNS after transplantation of fibroblasts modified with a regulatable vector. *Brain Res. Mol. Brain Res.* 126, 1-13.

Portas, C. M., Bjorvatn, B. and Ursin, R. (2000) Serotonin and the sleep/wake cycle: special emphasis on microdialysis studies. *Prog. Neurobiol.* 60, 13-35.

Rasmusson, D. D., Clow, K. and Szerb, J. C. (1992) Frequency-dependent increase in cortical acetylcholine release evoked by stimulation of the nucleus basalis magnocellularis in the rat. *Brain Res.* 594, 150-154.

Shackman, H. M., Shou, M., Cellar, N. A., Watson, C. J., Kennedy, R. T. (2007) Microdialysis coupled on-line to capillary liquid chromatography with tandem mass spectrometry for monitoring acetylcholine in vivo. *J. Neurosci. Methods* 159, 86-92.

Snyder, E. Y. and Senut, M. C. (1997) The use of normeuronal cells for gene delivery. *Neurobiolo Discuss.* 4, 69-102.

Svoboda, K. and Yasuda, R. (2006) Principles of two-photon excitation microscopy and its applications to neuroscience. *Neuron* 50, 823-839.

Palmer, A. E. and Tsien, R. Y. (2006) Measuring calcium signalling using genetically targetable fluorescent indicators. *Nature Protocols* 1, 1057-1065.

Tuszynski, M. H., Peterson, D. A., Ray, J., Baird, A., Nakahara, Y. and Gage, F. H. (1994) Fibroblasts genetically modified to produce nerve growth factor induce robust neuritic ingrowth after grafting to the spinal cord, *Exp. Neurol.* 126, 1-14.

Zhang, J., Hupfeld, C. J, Taylor, S. S, Olefsky, J. M. and Tsien, R. Y. (2005) Insulin disrupts □-adrenergic signalling to protein kinase A in adipocytes. *Nature* 437, 569-573.

Zhang, M.-Y., Hughes, Z. A., Kerns, E. H., Lin, Q. and Beyer, C. E. (2007) Development of a liquid chromatography/tandem mass spectrometry method for the quantitation of acetylcholine and related neurotransmitters in brain microdialysis samples. *J. Pharm. Biomed. Anal.* 44, 586-593.

The invention claimed is:

1. A method for measuring biochemical signaling molecules in vivo, comprising:

contransfecting neurofluocytes with cDNAs of a membrane receptor and a fluorophore to produce cotransfected neurofluocytes, wherein the cotransfected neurofluocytes emit an optical signal in response to detection of at least one target biochemical signaling molecule, and wherein the signaling molecule induces an intracellular change in an optical signal within the neurofluocytes;

implanting the neurofluocytes into live tissue; and monitoring the optical signal from the neurofluocytes using a microscope adapted for deep tissue imaging.

2. The method of claim 1, wherein the cotransfected neurofluocytes are produced from Human Embryonic Kidney cells.

3. The method of claim 1, wherein the neurofluocytes are selected from the group consisting of primary and immortalized fibroblasts, glial cells, peripheral neural tissue, and tumor-derived cells, or autologous cells created from Schwann cells, endothelial cells and astrocytes.

4. The method of claim 1, wherein the neurofluocytes are skin fibroblasts.

5. The method of claim 1, wherein the live tissue is an animal brain and the step of monitoring comprises:

performing a craniotomy to expose the animal brain; and immobilizing the animal;

wherein the microscope is a two-photon laser scanning microscope.

6. The method of claim 1, wherein the optical signal is generated by a FRET-based biosensor.

7. The method of claim 1, wherein the optical signal is generated by a fluorescent organic dye.

8. The method of claim 1, wherein the optical signal is generated by an optical reporter protein.

9. The method of claim 1, wherein a plurality of target biochemical signaling molecules are detected by producing a plurality of different neurofluocytes, each comprising fluorophores that emit different optical signals for each different target biochemical signaling molecule.

10. The method of claim 9, wherein the different optical signals are detected simultaneously.

11. A method for measuring neurotransmitters in vivo, comprising: producing neurofluocytes by co-transfecting host cells with cDNAs of a membrane receptor of a neurotransmitter and a tag that emits an intracellular optically-detectable signal in the presence of the signaling molecules; implanting the neurofluocytes into a brain of a live animal; monitoring the optically-detectable signal using a microscope adapted for deep tissue imaging.

12. The method of claim 11, wherein the step of monitoring comprises:

performing a craniotomy to expose the animal brain; and immobilizing the animal;

wherein the microscope is a two-photon laser scanning microscope.

13. The method of claim 11, wherein the neurofluocytes are produced from Human Embryonic Kidney cells.

14. The method of claim 11, wherein the neurofluocytes are selected from the group consisting of primary and immortalized fibroblasts, glial cells, peripheral neural tissue, and tumor-derived cells, or autologous cells created from Schwann cells, endothelial cells and astrocytes.

15. The method of claim 11, wherein the neurofluocytes are skin fibroblasts.

16. The method of claim 11, wherein the optical signal is generated by a FRET-based biosensor.

17. The method of claim 11, wherein the optical signal is generated by a fluorescent organic dye.

18. The method of claim 11, wherein the optical signal is generated by an optical reporter protein.

19. The method of claim 11, wherein a plurality of target biochemical signaling molecule are detected by producing a plurality of different neurofluocytes, each comprising fluophors that emit different optical signals for each different target biochemical signaling molecule.

20. The method of claim 19, wherein the different optical signals are detected simultaneously.

* * * * *

SEQUENCE LISTING

```
<160> NUMBER OF SEQ ID NOS: 2

<210> SEQ ID NO 1
<211> LENGTH: 1383
<212> TYPE: DNA
<213> ORGANISM: Rattus norvegicus
<221> NAME/KEY: gene
<223> OTHER INFORMATION: GenBank Accession No. NM_080773; Unigene:
      Rn.119395 cholinergic receptor, muscarinic 1 (Chrm1), mRNA

<400> SEQUENCE: 1

atgaacacct cagtgccccc tgctgtcagt cccaacatca ctgtcttggc accaggaaag      60

ggtccctggc aggtggcctt catcgggatc accacaggcc tcctgtctct agctacagtg     120
```

-continued

```
acaggcaacc tactggtact catctccttc aaggtcaaca ccgagctcaa gacagtcaac    180

aactacttcc tgctgagcct ggcctgtgct gacctcatca ttggcacctt ctccatgaac    240

ctctatacca cgtacctgct catgggccac tgggctctgg gcacactggc ctgtgacctc    300

tggctggccc tggactatgt ggccagcaac gcctctgtca tgaatcttct gctcatcagc    360

tttgaccgtt acttctcggt gacccgaccc ctgagctacc gagccaagcg cactccccga    420

agggcagctc tgatgattgg cctagcatgg ctggtttcct tcgttctctg ggccccagcc    480

atcctcttct ggcaatacct agttggggag cggacagtgc tggctgggca gtgctacatc    540

cagttcctct cccaacccat catcactttt ggcacagcca tggccgcctt ctacctccct    600

gtcacggtca tgtgtacact gtactggcgc atctaccggg agacagaaaa ccgagcccgg    660

gagctggccg ccctgcaggg ctctgagaca ccaggcaaag gtggtggcag cagcagcagc    720

tcagagaggt cacagccagg ggctgaaggc tcacccgagt cgcctccagg ccgctgctgc    780

cgctgttgcc gggcacccag gctcctgcag gcctacagct ggaaggaaga agaagaggag    840

gatgaaggct ccatggagtc cctcacatcc tccgaaggtg aggagcctgg ctcagaagtg    900

gtgatcaaga tgcccatggt agattctgaa gcacaggcac ccaccaagca gcctcccaaa    960

agctccccaa atacagtcaa gaggcccacc aagaaaggcc gagaccgagg cggcaagggc   1020

caaaaacccc gagggaagga acagctggcc aagagaaaga ccttctcact ggtcaaggag   1080

aagaaggcag ctcggaccct gagtgccatc ctgctggcct tcatcctcac ctggacacca   1140

tataacatca tggtgctggt atctaccttc tgcaaggact gtgttcctga aaccctgtgg   1200

gagctgggct actggctatg ctacgtcaac agcactgtca accccatgtg ctatgcactg   1260

tgcaacaaag ccttccggga cacgttccgc ctgctgctgc tctgccgctg ggacaagagg   1320

cgctggcgca agatccccaa gcgccctggc tctgtgcacc gcacccccctc ccgccaatgc   1380

taa                                                                 1383
```

```
<210> SEQ ID NO 2
<211> LENGTH: 2001
<212> TYPE: DNA
<213> ORGANISM: Rattus norvegicus
<221> NAME/KEY: gene
<223> OTHER INFORMATION: GenBank Accession No.
      NM_024394;5-hydroxytryptamine (serotonin) receptor 3a (Htr3a),
      mRNA.

<400> SEQUENCE: 2

aagcagcctg cctgggacat gaggttggca gcgggtgtgc aggctggcag tctgggggac     60

tcatcctgag tggctgctcc gaggccctcc cacatccggg aagcttgcca tgccgctctg    120

catcccgcag gtgctgttgg ccttgttcct ttccgtgctg atagcccagg gagaaggcag    180

ccggaggagg gccacccagg cccacagcac cacccagcct gctctgctga ggctgtcaga    240

tcacctcctg gctaactaca agaagggagt gcggcctgtg cgggactgga ggaagcccac    300

cctggtctcc attgatgtca tcatgtatgc catcctcaac gtggatgaga agaaccaggt    360

tctgaccacc tacatatggt accggcagtt ctggaccgac gagtttctac agtggactcc    420

tgaggacttc gacaatgtca ccaaattgtc catccccacc gacagcatct gggtccctga    480

catcctcatc aatgagtttg tggacgtggg gaagtctcca agcattcctt atgtgtatgt    540

gcaccatcaa ggtgaagtcc agaactacaa gcccctacag ctggtgaccg cctgtagcct    600

tgacatctat aacttcccgt tcgatgtgca gaactgctct ctgaccttca ccagctggct    660

gcataccatc caggacatca acatttccct gtggcgaaca ccagaagaag tgaggtcgga    720
```

-continued

```
caagagcatc ttcataaatc agggcgagtg ggagctgctg ggggtgttca ccaaatttca    780
ggagttcagt atagaaacca gtaacagcta tgcggaaatg aagttctacg tggtcatccg    840
ccggcggcct ttattctacg cagtcagcct cttgctgccc agtatcttcc tcatggtcgt    900
ggacattgtg ggcttttgtc tgcccccgga cagtggtgag agagtgtctt tcaagatcac    960
gctccttctg ggatactcag tctttctcat catcgtgtca gacacactgc ctgcaacggc   1020
catcggcact cccctcattg gtgtctactt tgtagtgtgc atggctctgc tggtgataag   1080
cctcgctgag accatcttca ttgtgcagct ggtgcataag caggatttac agcgccctgt   1140
acctgactgg ctgaggcacc tggtcctaga cagaatagcc tggctgctct gcctagggga   1200
gcagcccatg gcccataggc ccccagccac cttccaagcc aacaagactg atgactgctc   1260
agccatggga aaccactgca gccatgtcgg aagccctcag gacttggaga agacctcgag   1320
gagcagagat agccctcttc caccaccaag ggaggcctcg ctggctgtgc gtggcctctt   1380
gcaagagctg tcctccatcc gccactccct ggagaagcgg gatgagatgc gggaggtggc   1440
aagggactgg ttgcgggtgg gatatgtgct ggacaggctg ctgtttcgca tctacctgct   1500
ggccgtgctg gcttacagca tcaccctggt cacgctctgg tccatttggc attattcctg   1560
agtgggtaca gcctggcagg gaggggatgt gagtcctgca tcctgtttcc aacaccaatt   1620
catctgagca accccagtcc ccttgtcccc taaacttagc actgaagacc cggtcagacc   1680
ccccgacttc gctatcatgg ctttaaagca tgatatccta gatcaagagg aaccaagact   1740
cctctaactt attaagacat caagccctgg ttccttttcc agtacttctg tgattatggc   1800
ccttgggatg gctcatttcc acagtttttt tttccttttt gatcagagga aagcaaattc   1860
tcttgcctag gtgcctgaga cgtctgtgcc tgttttatcc aggccccagt ggcttcttct   1920
tcagctcact tgtgggtact tccctagcgc tcagcctcat caaccaacgg ggggagggga   1980
taataaaatg ctatgatatc c                                               2001
```